(12) United States Patent
Ciechanowski et al.

(10) Patent No.: US 9,610,216 B2
(45) Date of Patent: Apr. 4, 2017

(54) RESISTIVE ACTUATION UNIT FOR TUB SYSTEMS

(71) Applicant: C.G. AIR SYSTÈMES INC., Ste-Marguerite-de-Dorchester (CA)

(72) Inventors: Dominique Ciechanowski, Sainte-Marguerite-de-Dorchester (CA); Miguel Castellote, Sainte-Marguerite-de-Dorchester (CA)

(73) Assignee: C.G. AIR SYSTÈMES INC., Ste-Marguerite-de-Dorchester (CA)

( * ) Notice: Subject to any disclaimer, the term of this patent is extended or adjusted under 35 U.S.C. 154(b) by 51 days.

(21) Appl. No.: 14/520,883

(22) Filed: Oct. 22, 2014

(65) Prior Publication Data

US 2015/0033466 A1 Feb. 5, 2015

Related U.S. Application Data

(63) Continuation-in-part of application No. 13/456,790, filed on Apr. 26, 2012, now abandoned.

(Continued)

(51) Int. Cl.
*A61H 33/00* (2006.01)
*A61H 33/02* (2006.01)
(Continued)

(52) U.S. Cl.
CPC ....... *A61H 33/005* (2013.01); *A61H 33/0087* (2013.01); *A61H 33/0095* (2013.01); *A61H 33/02* (2013.01); *A61H 33/6089* (2013.01); *A61H 2033/0054* (2013.01); *A61H 2033/0083* (2013.01); *A61H 2201/10* (2013.01); *A61H 2201/102* (2013.01); *A61H 2201/5007* (2013.01); *A61H 2201/5028* (2013.01);
(Continued)

(58) Field of Classification Search
CPC .......... A61H 33/005; A61H 2033/0054; A61H 2033/0058; A61H 2033/0066; A61H 2033/007; A61H 2201/5046
USPC ...................................................... 200/600
See application file for complete search history.

(56) References Cited

U.S. PATENT DOCUMENTS

1,395,579 A 11/1921 Brooke
3,081,594 A 3/1963 Atkins
(Continued)

*Primary Examiner* — Erin Deery
(74) *Attorney, Agent, or Firm* — Norton Rose Fulbright Canada LLP (57) ABSTRACT

A tub comprising a body for holding a volume of water. A tub system is coupled to the body to perform a function on the volume of water. At least a first circuit has a first circuit portion comprising at least one resistive switch mounted to a visible surface of the body and comprising at least a first resistive element adapted to be contacted by a bather, second circuit portion comprising a water detection sensor mounted to the body for containing liquid in the body above a given level, the first circuit being open between the first resistive element and the water detection sensor, an actuating closed circuit condition by which a bather in liquid above the given level closes the first circuit between the first circuit portion and the second circuit portion when touching the first resistive element. A controller is operationally coupled to first circuit portion and the second circuit portion of the first circuit, and to the tub system, the controller adapted to detect the actuating closed circuit condition to trigger an action of the tub system.

11 Claims, 5 Drawing Sheets

Related U.S. Application Data (60) Provisional application No. 61/479,100, filed on Apr. 26, 2011.

(51) Int. Cl.
    *H01C 10/50* (2006.01)
    *A61M 21/00* (2006.01)
    *A61N 5/06* (2006.01)

(52) U.S. Cl.
    CPC .. *A61H 2201/5058* (2013.01); *A61H 2205/12* (2013.01); *A61M 2021/0016* (2013.01); *A61M 2021/0044* (2013.01); *A61N 2005/0663* (2013.01); *A61N 2005/0668* (2013.01); *H01C 10/50* (2013.01)

(56) References Cited

U.S. PATENT DOCUMENTS

| | | | |
|---|---|---|---|
| 3,629,780 A * | 12/1971 | Burcham | H01C 10/36 338/172 |
| 4,013,835 A | 3/1977 | Eachus et al. | |
| 4,353,552 A | 10/1982 | Pepper, Jr. | |
| 4,419,653 A * | 12/1983 | Waigand | G01L 1/20 338/114 |
| 4,716,605 A * | 1/1988 | Shepherd | A61H 33/0087 4/541.2 |
| 4,780,917 A | 11/1988 | Hancock | |
| 6,320,282 B1 | 11/2001 | Caldwell | |
| 6,476,363 B1 * | 11/2002 | Authier | A61H 33/0087 219/481 |
| 6,874,175 B2 * | 4/2005 | Laflamme | A61H 33/60 4/541.1 |
| 8,847,913 B2 * | 9/2014 | Tempas | A61H 33/005 178/18.05 |
| 9,063,623 B2 * | 6/2015 | Royhob | G06F 3/044 |
| 2001/0244103 | 12/2004 | Laflamme et al. | |
| 2009/0119832 A1 * | 5/2009 | Conroy | E03C 1/05 4/623 |

* cited by examiner

RESISTIVE ACTUATION UNIT FOR TUB SYSTEMS

CROSS-REFERENCE TO RELATED APPLICATION(S)

The present application is a continuation-in-part of U.S. application Ser. No. 13/456,790, filed Apr. 26, 2012, which claims priority on U.S. application Ser. No. 61/479,100, filed on Apr. 26, 2011, the contents of both of which are incorporated herein by reference.

FIELD OF THE APPLICATION

The present application relates to tubs having tub systems such as water massage systems (i.e., whirlpool systems), air-jet massage systems, aromatherapy systems, etc, and to an actuation unit for activating such tub systems.

BACKGROUND OF THE ART

Tubs are well known for their primary use, namely a washroom installation in which a user person washes and bathes. Tubs have, however, evolved to add relaxation and comfort to practicality, and are found in many forms, such as bathtubs, spas, whirlpools.

For instance, tubs are now provided with air-jet systems and whirlpool systems, by which air or water is injected into the water of the tub to create some turbulence in the water. The turbulence creates a massaging effect on the bather in the tub. Other types of electrically actuated systems, such as oxygenation systems, foot-massage systems and aromatherapy systems are provided in conjunction with tubs, whereby a plurality of treatments and physical/sensorial experiences are available with tubs. Such systems are often actuated through mechanical switches with normally-open contacts, which contacts are closed by the manipulation of the user.

Other types of systems have been developed to avoid the use of mechanical contacts. For instance, systems using touchless or finger-sensitive technologies, which operate based on capacitive field fluctuation. One drawback with such systems is their sensitivity to dielectric liquids, whereby they do not constitute an efficient solution for tub applications.

The bather having recourse to such treatments or physical/sensorial experiences seeks amongst other things a moment of relaxation. It is therefore desired to simplify the use of all such systems to ensure that the bather benefits from relaxing in the tub.

SUMMARY OF THE APPLICATION

It is therefore an aim of the present invention to provide a novel resistive actuation unit for tub systems.

In accordance with a first broad aspect, there is provided a tub comprising: a body for holding a volume of water; a tub system coupled to the body and adapted to perform a function on the volume of water; at least a first circuit having: a first circuit portion comprising at least one resistive switch mounted to a visible surface of the body and comprising at least a first resistive element adapted to be contacted by a bather, a second circuit portion comprising a water detection sensor mounted to the body for containing liquid in the body above a given level, the first circuit being open between the first resistive element and the water detection sensor, an actuating closed circuit condition by which a bather in liquid above the given level closes the first circuit between the first circuit portion and the second circuit portion when touching the first resistive element; a controller operationally coupled to first circuit portion and the second circuit portion of the first circuit, and to the tub system, the controller adapted to detect the actuating closed circuit condition to trigger an action of the tub system.

DESCRIPTION OF THE PREFERRED EMBODIMENTS

Figure 1:
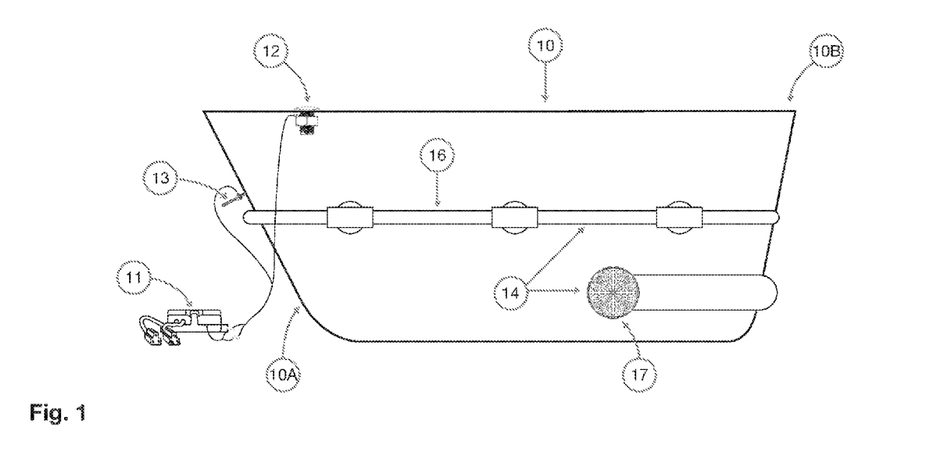
FIG. 1 is a schematic view of a tub with resistive actuation unit in accordance with an embodiment of the present disclosure, with a water detection sensor above piping.

Referring to the drawings and more particularly to FIG. 1, a tub 10 is generally illustrated. A hidden or inner surface of the tub 10, comprising the tub wall 10A, is shown, although this surface is typically not visible once the tub 10 is installed. A visible or outer surface of the tub 10, comprising a flange 10B, is also shown. The tub 10 is equipped with a resistive actuation unit featuring a controller 11 that is electrically actuated. The controller 11 is connected to one or more resistive switch devices 12 to send an actuation signal to the controller 11. The controller unit 11 may also be connected to a water detection sensor 13, to determine whether a liquid (e.g., water) is present in the tub 10 and to be part of a circuit with the resistive switch devices 12.

The controller 11 is used to operate a tub system 14. In the embodiment, the tub system 14 is a water jet system, by which water from the tub 10 is pressurized to be reinjected in the tub by jets. Alternative tub systems as in 14 may be used individually or in combination with the water jet system, such as air massage systems, oxygenation systems, foot-massage systems, chromotherapy systems, and aromatherapy systems, among numerous other possibilities. Accordingly, the functions or effects performed by the tub system 14 may comprise but are not limited to adjusting the temperature, the flow, and the pressure of the water, adjusting the pressure of the air injected in the water, modifying a scent diffused in the tub (in the case of aromatherapy systems), and modifying the lighting illuminating the tub (in the case of chromotherapy systems). In order to achieve various effects, a plurality of resistive switch devices 12 may thus be connected to the controller 11, each resistive switch device 12 being associated with a function of the tub system 14.

Figure 2:
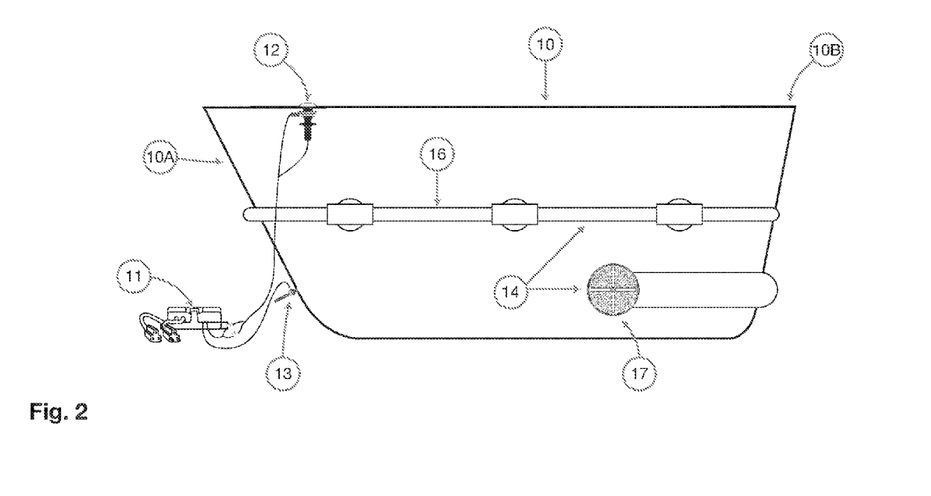
FIG. 2 is a schematic view of a tub with resistive actuation unit in accordance with an embodiment of the present disclosure, with a water detection sensor in a bottom of the tub.
Figure 3:
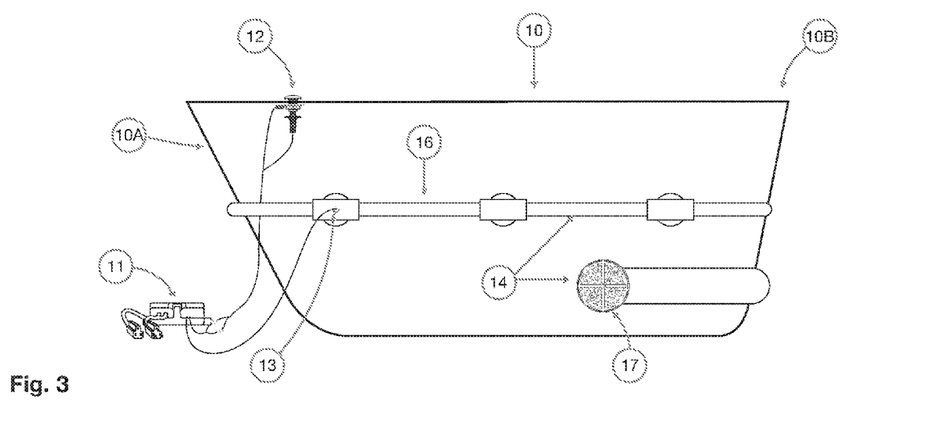
FIG. 3 is a schematic view of a tub with resistive actuation unit in accordance with an embodiment of the present disclosure, with a water detection sensor in piping.

The controller 11 is therefore the interface between the user and the tub system 14, as it is used to transmit actuation commands from the user to the tub system 14, to actuate or stop the tub system 14. Moreover, additional commands may be performed via the resistive actuation system, by providing additional resistive switch devices 12 (although not shown). Such additional commands include any appropriate function that may be performed by the tub system 14, and also the increase and decrease of the intensity of the effect performed by the tub system 14. The controller 11 may also perform safety functions, such as actuating the tub system 14 only when suitable operating conditions are met, such as the presence of water in the tub 10 beyond a given level, as per the positioning of the water detection sensor 13. Illustratively, if no water is in the tub 10 or the detected level of water is below a predetermined threshold, transmission by the user of an actuation command via the resistive switch devices 12 will not be possible as detailed below, and will not result in activation of the desired functions by the tub system 14. For that reason, as shown in FIG. 1, the water detection sensor 13 is located directly in the tub wall 10A (including the bottom wall of the tub 10). It is observed that the water detection sensor 13 may be positioned above the piping 16 of the tub system 14 to ensure that the level of water in the tub 10 is above the piping 16. Alternatively, as shown in FIG. 2, the water detection sensor 13 may be positioned below the piping 16 yet above the level of an inlet 17 of the tub system 14. Also, as illustrated in FIG. 3, the water detection sensor 13 may be located in the piping 16 of the tub system 14.

Figure 4:
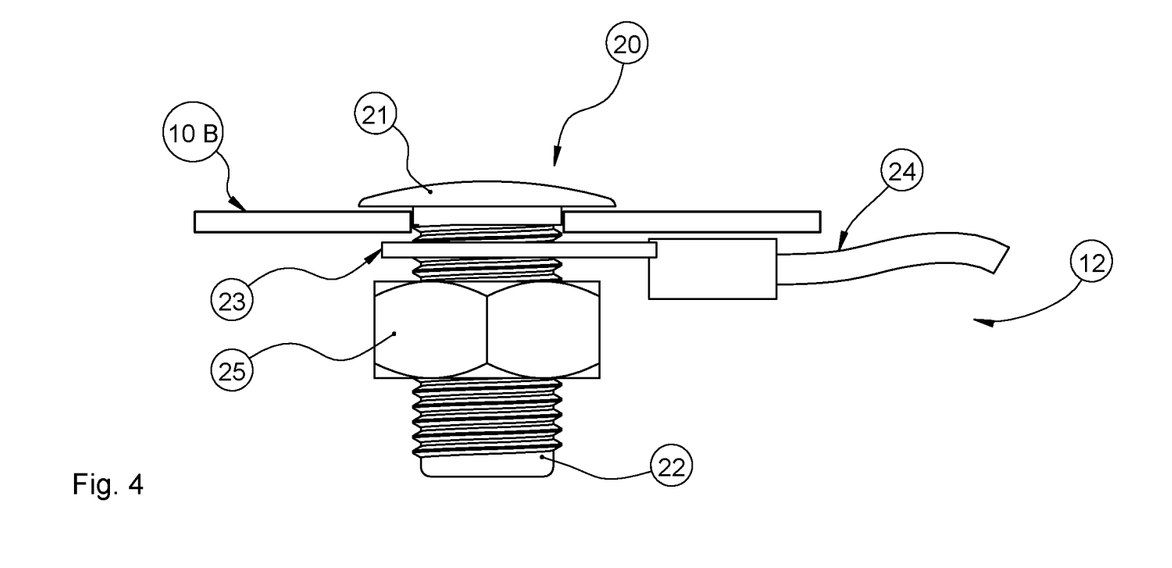
FIG. 4 is side view of a resistive switch device in accordance with a first embodiment of the present disclosure.

Referring to FIG. 4, one of the resistive switch devices 12 in accordance with a first illustrative embodiment will now be described. The switch device 12 comprises a first resistive element 20 comprising a head portion 21, which may be exposed on a visible face of the flange 10B of the tub 10. The head portion 21 may be provided with a shape, such as a pushbutton shape, suitable for actuation thereof by the user. The head portion 21 may be further provided with indicia or logo, drawn, etched, or otherwise presented thereon, which is indicative of the function that will be performed when a user presses the switch device 12.

The resistive element 20 may also comprise a bottom portion 22, which may feature threading thereon. A connector 23 may be coupled to the bottom portion 22 and is adapted to be connected to the controller 11 by a wire 24 or any other suitable means. The connector 23 may be an eyelet connector or any other appropriate connector known to those skilled in the art. A nut 25, which may feature thereon tapping adapted to threadingly engage with the threading provided on the bottom portion 22, may be coupled to the bottom portion 22 for maintaining the connector 23 in contact with the head portion of the resistive element 20. Any appropriate connection configuration may be used to ensure that the connector 23 remains in contact with the bottom portion 22, and that the resistive element 20 remains secured to the tub wall 10A (e.g., adhesives, mating engagement, etc).

In operation, the resistive element 20 may be positioned on the flange (or generally horizontal wall) 10B of the tub 10 by inserting the bottom portion 22 in a hole shown in FIG. 4, machined or manufactured in the flange 10B. When in place, the head portion 21 of the resistive element 20 illustratively rests on a visible face of the flange 10B of the tub while the bottom portion 22 projects into an underside of the tub 10. The connector 23 may then be coupled to the bottom portion 22 in abutment with a hidden face of the flange 10B. The nut 25 may be coupled to the bottom portion 22 in abutment with the connector 23 to secure the latter in place. The connector 23 may further be connected to the controller 11 via the wire 24 such that a current may circulate in the resistive element 20 via the wire 24, when the circuit incorporating the resistive element 20 is closed, as described herein below.

Figure 5:
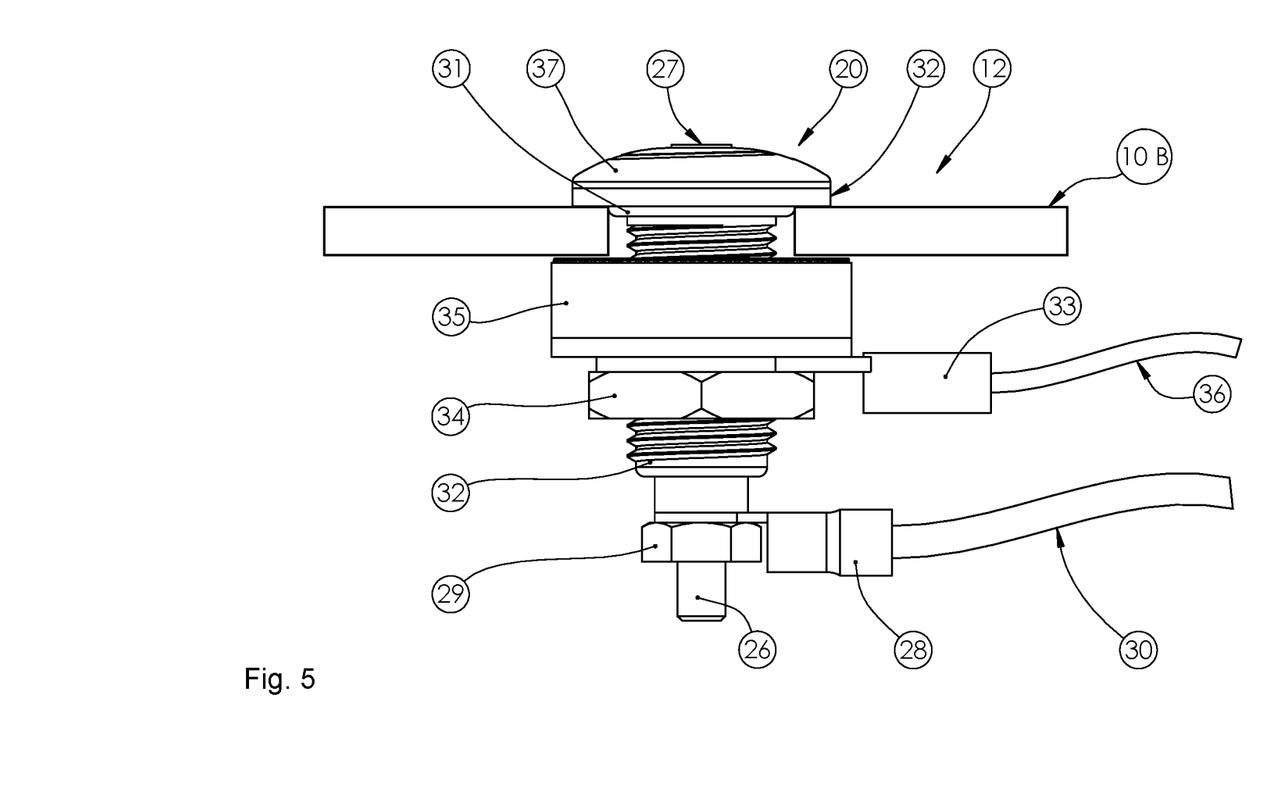
FIG. 5 is side view of a resistive switch device in accordance with a second embodiment of the present disclosure.

Referring to FIG. 5 in addition to FIG. 4, since the head portion 21 of the first resistive element 20 may be exposed on the visible face of the flange 10B, the first resistive element 20 may be sensitive to the contact of water. As such, the controller 11 may falsely identify a command when water is in contact with the head portion 21 of the resistive element 20, as detailed below. In order to prevent inadvertent activation of the tub system 14 due to water accidentally contacting the first resistive element 20 without the user contacting the latter, a second resistive element may therefore be provided in electrical insulation with the first resistive element 20. In this manner, it may be possible to discriminate between user activation of the resistive switch device 12 and water contacting the resistive switch device 12. However, in some applications, for instance in which the switch device 12 is minimally exposed to water, the use of a single resistive element suffices.

Figure 6:
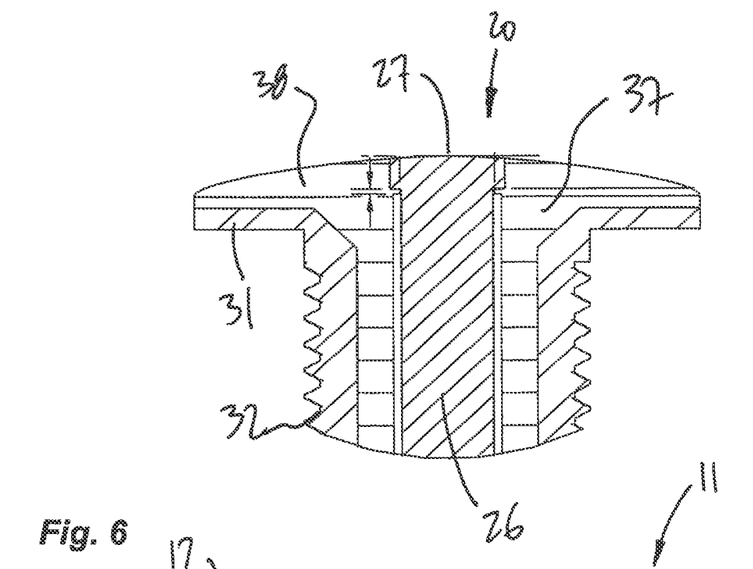
FIG. 6 is a sectional view of a portion of the resistive switch device of FIG. 5.

Referring concurrently to FIGS. 5 and 6, according to a second illustrative embodiment, the first resistive element 20 may have a slender rod 26, having an exposed tip portion 27, being exposed on the visible face of the flange 10B of the tub 10. A bottom of the rod 26 of the element 20 projects into an underside of the tub 10, and may feature threading thereon. An eyelet connector 28 (or any other appropriate connector) is maintained in contact with the rod 26 by way of nut 29, or by any appropriate connection configuration (e.g., fastener, glue, magnets, etc.). The connector 28 is connected to the controller 11 by wire 30, through which a current circulates to modify the value of the resistive element 20 detected by the controller 11 in the event of a user contacting the tip portion 27.

A second resistive element is illustratively provided and comprises a ring portion 31 that is exposed on the visible face of the flange 10B of the tub 10. A sleeve 32 is in conductive relation with the ring portion 31. The sleeve 32 may comprise threading, as shown in FIGS. 5 and 6.

A connector 33 is in contact with the outer surface of the sleeve 32 and is maintained in the illustrated position by way of a nut 34, or by any appropriate connection configuration (e.g., fastener, glue, magnets, etc.).

A sealing ring 35 is positioned about the sleeve 32 in abutment with the hidden face of the flange 10B. The sealing ring 35 seals the hole in the tub 10 through which passes the sleeve 32. Nut 34 is used to press the sealing ring 35 against the hidden face of the flange 10B of the tub 10. The connector 33 is connected to the controller 11 by wire 36. Although not shown, the resistive switch device 12 of FIG. 4 may have a similar sealing arrangement, with a sealing ring 35 and fastener.

An insulating spacer 37 connects the first resistive element 20 to the second resistive element 31/32. The insulating spacer 37 is illustratively a T-shaped member with an inner channel accommodating part of the rod 26. Moreover, the sleeve 32 houses a portion of the spacer 37, as shown in FIG. 6. The insulating spacer 37 has a head portion 38. The head portion 38 is typically provided with an appropriate indicia or logo to indicate the function that will be performed when pressing the resistive switch device 12. Alternatively, the indicia or logo may be on the tip portion 27 of the first resistive element 20. In an embodiment, the periphery of the ring portion 31 does not extend radially beyond a periphery of the head portion 38. Accordingly, from a top plan view, the ring portion 31 is fully concealed under the head portion 38, as observed from FIG. 6.

Accordingly, a current may circulate in the second resistive element via the wire 36 when the circuit is closed, as detailed herein below.

Figure 7:
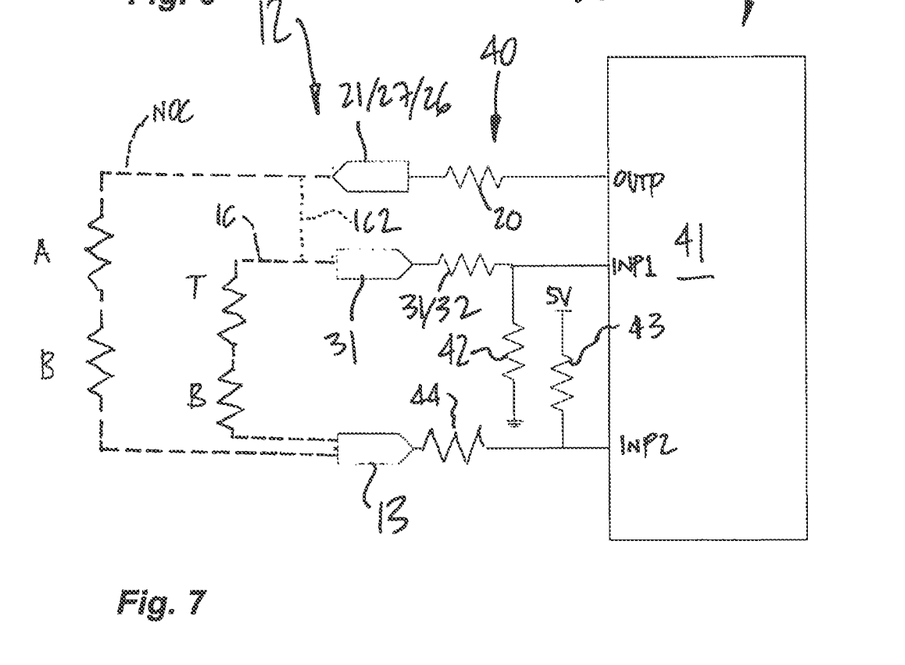
FIG. 7 is a schematic view of a circuitry of the resistive actuation unit of FIG. 3.

As shown in FIG. 7, a contemplated circuitry 40 and micro-processor 41 (or like circuitry or device) are shown, as used by the controller 11 to operate the resistive switch device 12. The circuitry 40 is similar whether it is for the resistive switch of FIG. 4 or of FIGS. 5 and 6, with the circuit portion or branch featuring the second resistive element 31/32 operational and/or present only when the resistive switch device 12 of FIGS. 5 and 6 is used. It is pointed out that any appropriate circuitry may be used as well and that switch devices 12 other than resistive may be used, as will be apparent to a person skilled in the art. However, considering that water is in the proximity of the resistive actuation unit, all necessary precautions must be taken to avoid any electrical shock. The use of resistive actuation is appropriate in that low current and low voltage are sufficient to operate the switch devices 12. Nevertheless, any appropriate safety circuit and ground must be present in the controller 11. Resistors 42 and 43 provide pull-down and pull-up functions respectively as described in the next paragraphs.

In order for the circuit to be closed, water B must be in the tub 10 in such a way that the sensor 13 is submerged, and the bather A in the tub water must touch the resistive switch device 12. A first circuit portion of the first circuit, namely from the controller 11 to the first resistive element 20, is conductively related to a second circuit portion of the first circuit portion, i.e., from the controller 11 to the sensor 13, by the bather A and water B. In doing so, the circuit is closed, i.e., an actuating closed circuit condition is reached, and the micro-processor 41 receives a current signal from the closing of the circuit, indicating a desired interaction from the bather. The resistance of the resistive elements 21, 27 and 31 is negligible in the circuit comparatively to the resistance of the human body and of the water. More specifically, a logical signal of 0 (close to 0 volts) is applied by the microprocessor 41 output pin OUTP to the resistive element 20, as shown by the circuit of FIG. 7. If the water detection sensor 13 does not receive this signal, the circuit is open. Hence, if the circuit is open, the input pin INP2 on the microprocessor 41 will be presented with a voltage level representative of the action of pull-up resistor 43 (illustrated as 5V for example).

On the other hand, in normal operating condition or actuating closed circuit condition, illustrated by path NOC (normal operating condition) in FIG. 7, if the bather A in the tub 10 touches the resistive element 20 and more particularly the head portion 21 (FIG. 4) or the exposed tip portion 27 (FIG. 6), the signal reaches the sensor 13, as a very low level current that passes through the body of the bather A and through bath water B, which creates a voltage divider. The microprocessor 41 will no longer read the given voltage value of 5 volts on input pin INP2 (i.e., based on the action of the pull-up resistor 43 in the open first circuit), but rather a voltage level determined by the voltage divider created. This is interpreted by the microprocessor 41 as a desired interaction, i.e., the occupant pressing the button, whereby the microprocessor 41 commands the controller 11 (e.g., to start/stop a bath effect, etc).

In the case of the embodiment of FIGS. 5 and 6, the second resistive element 31/32 (an other circuit portion) is used to prevent actuation in the case of a water trickle T, as shown by path IC (inhibit closed circuit condition), and is part of a second circuit. If there is no continuous water trickle between the resistive element 31/32 and bath water B, the measured voltage level at pin INP1 of microprocessor 41 will be close to zero volt due to action of pull-down resistor 42. However, if there is a continuous water trickle between the resistive element 31/32 and the bath water B, as shown by T in path IC of FIG. 7, the second circuit between terminals 13 and 31 closes and voltage at pin INP1 of microprocessor 41 will no longer be zero volt but rather a value determined by the voltage divider created. In such a case, the microprocessor 41 will not interpret this voltage value as being a desired interaction and will inhibit normal operation of the circuit, or prevent any action trigger.

This is also true if the water trickle exists between terminals 21 and 31 (at switch device 12) and a bather is present, in a further inhibiting closed circuit condition. In that case, the circuit between the terminals 31 and 13 is closed through path IC2 and presence of a bather A and bathing water B. The voltage at pin INP1 of microprocessor 41 will no longer be zero volt but rather a value determined by the voltage divider created. The microprocessor 41 will not interpret this voltage value as being a desired interaction and will inhibit normal operation of the circuit. Hence, the arrangement of FIG. 7 with a pair of circuits may require that the sensor be dried off before using the switches shown.

Therefore, in operation, when the second resistive element 31/32 forms a closed circuit with water sensor 13 through bath water B and water trickle T, a blocking condition is created in microprocessor 41 preventing further actions to take place. This blocking condition is managed by the software that is executed by microprocessor 41 and can only be removed by discontinuing the water trickle therefore opening the circuit between element 31/32 and sensor 13. Normal operation can then resume by action of a bather touching resistive element 20.

While FIG. 7 provides one example of a possible arrangement that may be used in accordance with the present disclosure, it should be pointed out that FIG. 7 is provided as an exemplary embodiment and that other configurations of circuit may be used as well.

In essence, FIG. 7 demonstrates a circuit that is closed by the bather A and the bath water B, which closed circuit is monitored by the controller 41 to trigger actions. Moreover, the arrangement of FIG. 7 (with or without two distinct circuits to avoid triggering actions by a water trickle T) with voltage dividers is one possible way to embody the claimed invention. Stated differently, the present disclosure relates to the concept of having a circuit closed by the presence of an occupant in a bathing tub while including provisions to prevent unintentional activation of the circuit when exposed to undesired presence of water trickle. The circuit nonetheless involves a water body and current circulating through the bather A, whereby all necessary measures must be taken in completely preventing any risk of electrical hazard.

The invention claimed is:

1. A tub comprising:
    a body for holding a volume of water;
    a tub system coupled to the body and adapted to perform a function on the volume of water;
    at least a first circuit having:
        a first circuit portion comprising at least one resistive switch mounted to a visible surface of the body and comprising at least a first resistive element adapted to be contacted by a bather,
        a second circuit portion comprising a water detection sensor mounted to the body, the water detection sensor detecting water in the body above a given level, the first circuit being open between the first resistive element and the water detection sensor, an actuating closed circuit condition in which a bather in the water of the body, the water being above the given level, closes the first circuit between the first circuit portion and the second circuit portion when touching the first resistive element, the first circuit including the first circuit portion, the second circuit portion, and configured to include the water in the body above the given level and the bather in the water when contacting the first resistive element;

a controller operationally coupled to first circuit portion and the second circuit portion of the first circuit, and to the tub system, the controller adapted to detect the actuating closed circuit condition to trigger an action of the tub system.

2. The tub of claim 1, further comprising:

at least a second resistive element insulatively coupled to the first resistive element; and a second circuit having an other circuit portion connected to the second resistive element, and an inhibiting closed circuit condition in which a water trickle contacting the second resistive element and the water above the given level closes the second circuit between the other circuit portion and the second circuit portion, the second circuit including the other circuit portion, the second circuit portion, and configured to include the water in the body above the given level and the water trickle between the second resistive element and the water in the body;

wherein the controller is operationally coupled to the other circuit portion, the controller adapted to detect the inhibiting closed circuit condition to block any action trigger of the tub system.

3. The tub of claim 2, wherein the first resistive element comprises a rod having a first end portion exposed on the visible surface of the body and a second end portion projecting into an underside of the body.

4. The tub of claim 3, wherein the second resistive element comprises a ring insulatively coupled to the first end portion of the rod so as to be exposed on the visible surface of the body.

5. The tub of claim 4, wherein the second resistive element further comprises a sleeve coupled to the second end portion of the rod in conductive relation with the ring.

6. The tub of claim 5, further comprising an insulating spacer housed in the sleeve and having an inner channel accommodating the rod therein, thereby insulatively coupling the first and second resistive elements.

7. The tub of claim 6, wherein the insulating spacer comprises a head portion exposed on the visible surface of the body.

8. The tub of claim 4, wherein the visible surface of the body comprises a generally horizontal wall and further wherein the at least one resistive switch is received in a hole formed in the horizontal wall with the ring in abutment with a visible face of the horizontal wall.

9. The tub of claim 5, further comprising a sealing ring positioned about the sleeve in abutment with a hidden face of a flange for sealing the hole.

10. The tub of claim 1, wherein the at least one resistive switch comprises a plurality of resistive switches each associated with a corresponding one of a plurality of functions of the tub system.

11. The tub of claim 2, wherein the controller is configured to detect a further inhibiting closed circuit condition when the first resistive element and the second resistive element are conductively joined to block any action triggering of the tub system.

* * * * *